United States Patent
Komulainen et al.

(10) Patent No.: US 6,849,851 B2
(45) Date of Patent: Feb. 1, 2005

(54) METHOD FOR CONTROLLING QUALITY AND CONDITION ON THE BASIS OF THERMAL IMAGING

(75) Inventors: Antti Komulainen, Keuruu (FI); Kari Juppi, Palokka (FI); Pertti Aimonen, Pirkkala (FI)

(73) Assignee: Metso Paper Automation Oy, Tampere (FI)

( * ) Notice: Subject to any disclaimer, the term of this patent is extended or adjusted under 35 U.S.C. 154(b) by 94 days.

(21) Appl. No.: 10/142,446

(22) Filed: May 10, 2002

(65) Prior Publication Data

US 2002/0166970 A1 Nov. 14, 2002

(30) Foreign Application Priority Data

May 11, 2001 (FI) ............................................. 20010989

(51) Int. Cl.$^7$ ................................................. G01J 5/02
(52) U.S. Cl. ....................................................... 250/340
(58) Field of Search .......................................... 250/340

(56) References Cited

U.S. PATENT DOCUMENTS

| | | | | | |
|---|---|---|---|---|---|
| 4,389,575 A | * | 6/1983 | Cole | ..................... | 250/559.47 |
| 5,086,220 A | * | 2/1992 | Berthold et al. | ....... | 250/559.01 |
| 5,358,606 A | | 10/1994 | Makkonen | .................... | 162/49 |
| 5,696,591 A | | 12/1997 | Billhorn et al. | ............. | 356/429 |
| 5,960,374 A | | 9/1999 | Lausier | ........................ | 702/81 |
| 5,990,468 A | | 11/1999 | Corneujots | ............... | 250/208.1 |
| 6,188,077 B1 | * | 2/2001 | Lind | ..................... | 250/559.01 |

FOREIGN PATENT DOCUMENTS

| | | | | |
|---|---|---|---|---|
| WO | WO 99/28730 A2 | * | 6/1999 | .......... G01N/21/89 |
| WO | WO 00/45156 A1 | * | 8/2000 | .......... G01N/21/89 |

OTHER PUBLICATIONS

Infrared Thermography—An Aid to Solving Paper Machine Moisture Profile Problems, Vickery, Dennis E., Tappi;, Dec. 1978 vol. 61, No. 12; pp. 17–20.

* cited by examiner

*Primary Examiner*—Constantine Hannaher
(74) *Attorney, Agent, or Firm*—Steinberg & Raskin, P.C.

(57) ABSTRACT

A method in the process of manufacturing and/or finishing a fiber web (11), in which method the Continuous and moving web (11), and/or a moving device (16, 17) related to the processing of the web (11), is monitored by one or more thermal cameras (10) of the infrared range or a corresponding detector/detectors for the purpose of controlling the quality or condition. A substantially continuous two-dimensional thermal image or continuous thermal chart (20) of an object (11, 16, 17) being monitored and in a propagating and/or rotating movement is formed by said detector/detectors in a time-resolved manner and in synchronization with the movement of the object (11, 16, 17) in the direction of the movement. To determine the properties of the object (11, 16, 17) and/or to detect defects in the object from the continuous thermal chart (20), local deviations and/or discontinuities (21, 22) in the temperature, particularly in the direction of movement are detected, and the cause of said deviations and/or discontinuities (21, 22) is identified on the basis of the periodicity of said phenomena in the direction of movement.

15 Claims, 2 Drawing Sheets

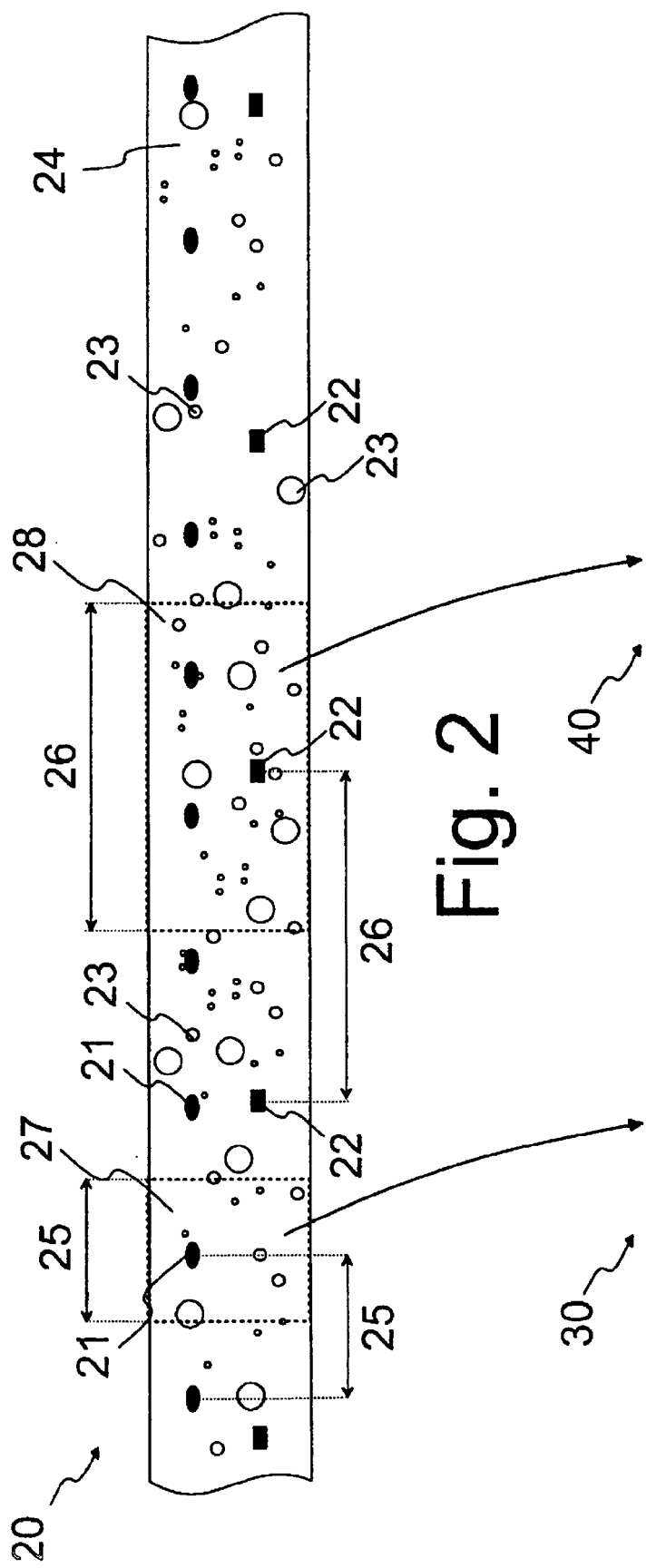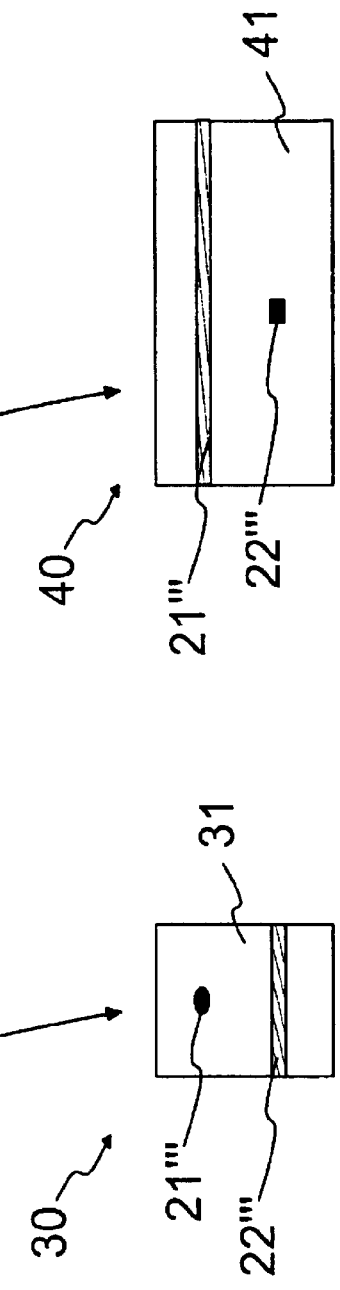

METHOD FOR CONTROLLING QUALITY AND CONDITION ON THE BASIS OF THERMAL IMAGING

FIELD OF THE INVENTION

The invention relates to a method for controlling quality and condition on the basis of thermal imaging, to be used in connection with processes of manufacturing and/or finishing a continuous fibre web.

BACKGROUND OF THE INVENTION AND PRIOR ART

With improved technology and usability of thermal cameras, they are being increasingly used in various industrial condition and quality control applications. Conventionally, thermal imaging has been used for monitoring the condition of various apparatus components. Typical uses have included, for example, the monitoring of the condition of various engines and bearings at intervals. By means of thermal imaging, defects in components can be detected in a contactless manner, for example as an increase in the surface temperatures of the components.

In paper industry, thermal imaging has also been applied to measure properties of the fibre web to be manufactured and/or processed, various rolls, as well as reels formed of the web, by methods which will be discussed in more detail below.

Article "Infrared Thermography—An Aid to Solving Paper Machine Moisture Profile Problems" (D. E. Vickery, J. E. Luce and W. Atkins, Tappi Journal, December 1978, Vol. 61, No. 12, pp. 17–20) discloses the use of a portable thermal camera for determining the moisture profile of the web in the cross-machine direction. According to the article, the temperature profile of the web in the cross-machine direction correlates clearly with the moisture profile of the web in the cross-machine direction, wherein for example wet streaks in the web in the machine direction are detected in a thermogram as streaks cooler than their environment. Said article also presents the use of a portable thermal camera for monitoring the condition of rotating machine components, such as rolls. In the determination of the temperature profile of said components in the cross-machine direction of the web, the temperature differences are detected as band-like temperature areas surrounding said rotating means.

The applicant's previous public patent application WO 00/45156 discloses a more sophisticated monitoring method, in which the monitoring of the moving web is implemented not only with a portable thermal camera but with one or more stationary thermal cameras for imaging the web in a continuous manner. Instead of control measurements to be taken at random or at regular intervals, the method described in WO 00/45156 is intended to be used for continuous monitoring of the web, particularly in connection with the coating of the web. A thermogram is displayed on one or more monitors to the user who can observe the process to be controlled substantially in real time, wherein, on the basis of phenomena detected in thermograms, the process to be controlled can be adjusted, if necessary, to optimize the process. The thermogram can also be recorded in a memory for later viewing.

However, the above-presented prior art methods utilizing a thermal camera involve the problem that the information contained in the thermal images is primarily analyzed by the user viewing the images. Thus, the user must have expertise and experience to find out the real cause of the phenomenon detected in the thermal images each time. For this reason, some of the information contained in the thermal images may also easily remain unutilized.

Furthermore, the solutions of prior art involve the problem that transient phenomena which may also occur only recurrently are easily disregarded by the user. In particular, phenomena which are very low in intensity and occur only recurrently in thermograms are very difficult to be detected by the human eye. In practice, the user will typically only see the average temperature profile of the object in the cross-machine direction in thermograms recorded according to prior art. For example, in the case of rolls, the problems are detected as band-like temperature areas surrounding the roll, and their cause cannot be found out on the basis of the measurement results in a fast and reliable way. In the machine direction, only such slow and trend-like temperature changes are detected, in which, for example, the temperature of the web at the measuring point is changed, for some reason, as a function of time in a more permanent manner.

To locate a malfunctioning component in the apparatus for manufacturing or processing the web, measurements according to prior art must be typically taken at several points in the process, which requires either the use of several thermal cameras placed in a stationary manner at different locations in the process, or taking the corresponding measurements by using a portable thermal camera. The first-mentioned method has the disadvantage of high equipment costs caused by the cameras, whereas the latter method has the disadvantage of slowness and poor repeatability of the manual measurements.

Basic Principle and Most Important Advantages of the Invention

The primary aim of the present invention is to provide a novel method for the control of quality and condition on the basis of thermal imaging, to be used in processes of manufacturing and/or finishing a continuous fibre web.

The aim of the invention is to make it possible to gather information about an object to be measured in a considerably more versatile and more detailed way than in methods of prior art, and further to analyse the measurement results automatically by means of computer image processing, which is significantly more efficient than methods of prior art. Thus, the invention makes it possible to implement a highly automated control of quality and condition.

By means of the invention, it is also possible to detect transient phenomena which occur only momentarily in the machine direction and which have been, until now, impossible to determine by methods of prior art. Another very significant advantage of the invention is that the cause of failures in the process can now be identified by means of the invention in an easier and more reliable way than in prior art.

The essential basic idea of the invention is that a two-dimensional thermal image, i.e. a thermal chart, of a measurable moving object is recorded by a thermal camera in a continuous manner so that said continuous thermal chart is synchronized in time with the movement of the object to be measured.

Consequently, by means of time-resolved thermal imaging, a location-resolved thermal chart, substantially continuous in the machine direction, is formed of the surface of the object to be imaged. In this thermal chart, for example areas corresponding to different points on the surface of the fibre web are shown in a location-resolved manner both in the cross-machine direction and in the machine direction.

Now, the synchronization of the two-dimensional thermal chart with the movement of the object will further make it possible to detect from the thermal chart, in an efficient and, if necessary, automatic way, recurrent and transient phenomena in the machine direction, and furthermore, the causes of these recurrent phenomena can be identified on the basis of the periodicity of the phenomena.

If the object to be imaged is, for example, a moving fibre web, the cause of a defect recurring at regular intervals in the web can be identified as a roll rotating at a known peripheral speed in relation to the web, wherein a damaged or soiled point on the surface of the roll causes a defect in the passing web, recurring at intervals corresponding to the peripheral length of said roll.

In an advantageous embodiment of the invention, the thermal chart formed of the object is averaged, in the machine direction, over a record length specific to the object to be monitored, to detect periodical phenomena of lower intensity. The record length to be used in the averaging can be selected to correspond, for example, to the peripheral length of a specific roll. The averaging will efficiently eliminate random noise which is present in thermal images and is generated, for example, in a situation in which the imaging is disturbed by water mist or water spraying occurring at random between the camera and the object to be imaged.

Using the method according to the invention, it is possible to look for phenomena which recur periodically in the thermal chart and are caused by the object itself to be imaged, or by a component preceding it in the process. Thanks to the imaging at good sensitivity in the infrared range, and averaging, it is also possible to detect periodical phenomena in the fibre web which are caused by (preceding) components located farther away from the point of imaging. As a result, it is possible to monitor more steps in the process (a longer web length) by using only a single measuring point.

The method according to the invention can be applied for monitoring the moving web itself, or for monitoring the condition of rotating/moving means which are involved in the processing of the web and are in contact with it, such as rolls and various textures (wires, felts). The invention is also applicable for monitoring the properties of reels to be formed of the web.

The malfunction of a means involved in the processing of the fibre web can be detected either by direct imaging of said means or on the basis of a marking caused by said means in the passing web.

The following more detailed description of the invention to be explicated will examples will more clearly illustrate, for anyone skilled in the art, advantageous embodiments of the invention as well as advantages to be achieved with the invention in relation to prior art.

BRIEF DESCRIPTION OF THE DRAWINGS

In the following, the invention will be described in more detail with reference to the appended drawings, in which FIG. 2 illustrates a continuous thermal chart formed according to the invention in principle, FIG. 3 shows, in principle, a matched thermal chart obtained from the continuous thermal chart of FIG. 2 by averaging across a given interval, and FIG. 4 shows, in principle, a matched thermal chart obtained from the continuous thermal chart of FIG. 2 by averaging across another interval.

DETAILED DESCRIPTION OF THE INVENTION

Figure 1:
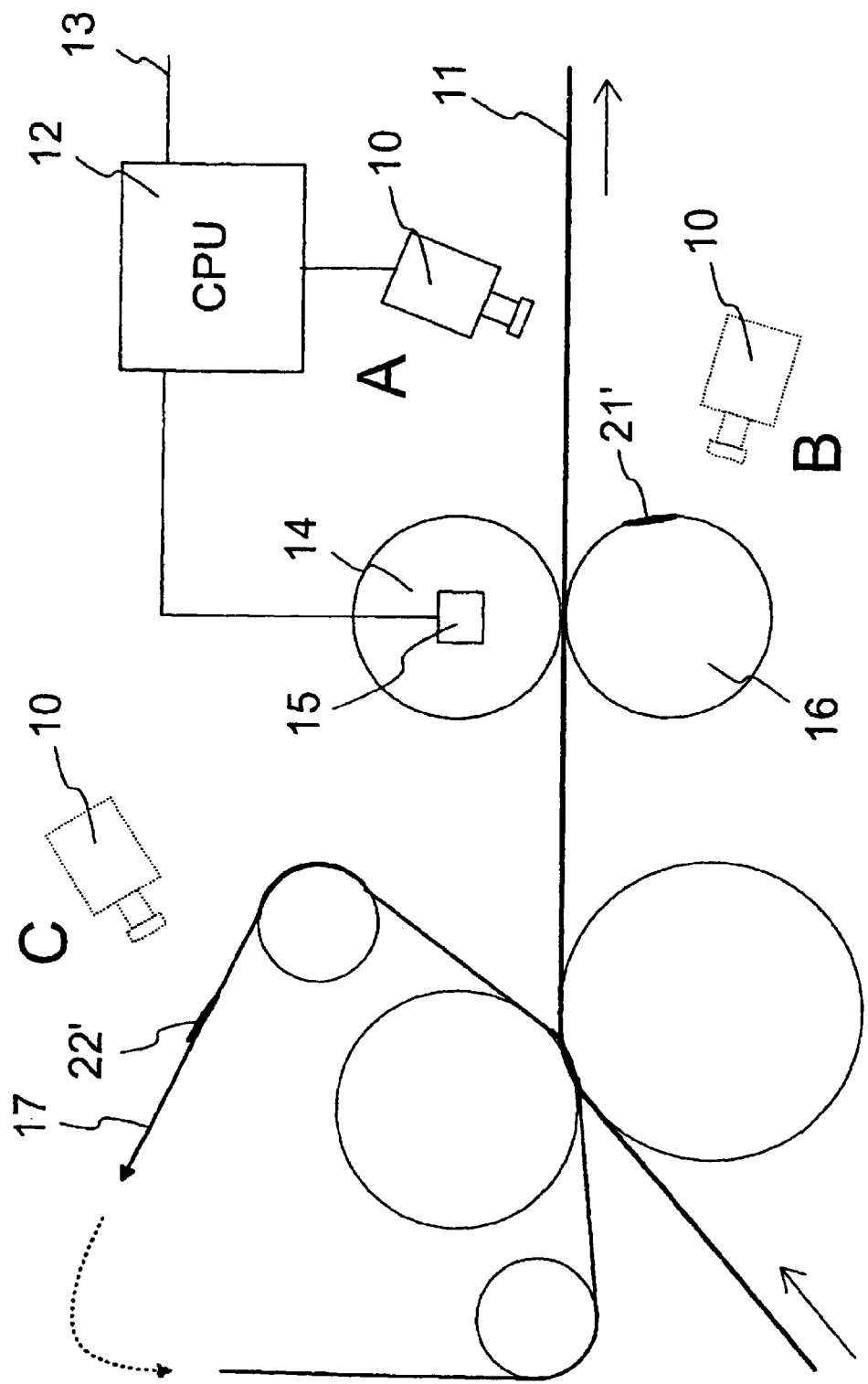
FIG. 1 shows some possible embodiments of the invention in principle.

FIG. 1 shows, in principle, some possible embodiments of the invention which correspond to different positions A, B and C of a thermal camera indicated in FIG. 1.

A thermal camera 10 located in the position A is arranged to image a moving web 11 as the object of measurement, to form a continuous thermal chart of the web 11 in accordance with the invention. The web 11 can be a fibre web present in various forms in paper or board manufacture, and depending on the location of the measurement, the web can also be supported at the imaging point by a wire, a roll or another means on the side opposite to the imaging direction.

The thermal camera 10 can be a conventional infrared camera which is based on the use of a single detector element and in which a rotating mirror or a corresponding arrangement is used to direct infrared radiation from the object to the infrared-sensitive detector element by the scanning principle. In other words, the measuring range detected by the detector element is continuously moved by scanning in the cross-machine direction of the web 11 along the web 11, wherein the temporally varying signal generated by the detector element can be used to form a substantially continuous two-dimensional thermal chart of the web 11 as the web moves forward in the direction indicated by arrows in FIG. 1.

The continuous thermal chart according to the invention is thus formed of the object 11 by temperature profiles in the direction transverse to the direction of its movement, recorded at successive moments of time. In the thermal chart, the areas corresponding to different points on the surface of the web 11 are indicated in a point-resolved manner both in the cross-machine direction and in the machine direction.

In modern, commercially available thermal cameras based on the use of a single detector element, the scanning rate can be, for example, 7000 scannings per second, and if desired, the scanning can be made unidimensional, always occuring at the same point of the image area. In other words, the camera repeatedly scans the same transverse line of the "image", wherein the function of the camera corresponds, in practice, to the function of a line indicator. Thus, in spite of even a high speed of the web 11 (for example, 1800 m/min), a continuous thermal chart can be formed of the web 11 with a good point resolution, thanks to said good time resolution.

Now, in contrast with the thermal imaging of prior art, the two-dimensional thermal chart imaged with a good time resolution can also be used to detect transient phenomena which occur only momentarily in the machine direction.

Instead of a single detector element and mechanical scanning of a measuring beam, the thermal camera 10 can also be based on the use of a line or matrix indicator. A line indicator, i.e. a unidimensional matrix detector, can be used, by applying suitable optics without mechanical scanning, to record "lines" of the object measured in its cross-direction successively in time, which lines can further be used to form a substantially continuous thermal image. Using a two-dimensional matrix detector, and the exposure and reading rate of the detector being sufficiently fast in relation to the movement of the object, the surface area of the object can be covered by recording two-dimensional thermal images at suitable intervals. These two-dimensional thermal images can further be used to compose a substantially continuous thermal image by placing the images one after the other in such a way that the "upper edge" of the preceding image is always aligned with the "lower edge" of the next image. To form a continuous thermal image, it is also possible to run a two-dimensional matrix indicator in a so-called line camera mode, wherein only one or a number of single lines of a two-dimensional matrix are read in a quick manner. Thus, the operation of the matrix indicator will, in practice, resemble the operation of one or more line indicators.

Advantageously, it is possible to use as the thermal camera 10 so-called bolometric infrared matrix cameras operating without separate nitrogen cooling, for example cameras based on the CMOS technology, or more sensitive cameras based on so-called quantum well technology.

The operating wavelength range of the thermal camera 10 is, within the infrared range, 0.8 to 12 micrometres, preferably for example 3 to 12 micrometres. The thermal camera 10 can also be arranged to operate on two or more narrower wavelength bands within said wavelength range, to detect interesting phenomena in a more efficient way and/or to reduce the effect of factors interfering with the imaging.

The thermal camera 10 is connected to a data processor 12 to record the image information in the memory of the data processor 12 and further to produce a continuous two-dimensional thermal chart in said memory. The data processor 12 can be, for example, a microcomputer or the like, which is equipped with suitable software, such as image processing software, for analyzing the information contained in the thermal chart totally or partly automatically.

Further, the data processor 12 may be arranged in a data transmission connection 13 with the other parts of the apparatus controlling the processing of the web 11. This makes it possible, for example, to make adjustments automatically on the basis of measurement results determined from the thermal chart. By means of the data transmission connection 13, it is also possible to implement the alarming of the user or other measures when certain predetermined limit values are exceeded.

Preferably, the data processor 12 is equipped with a user interface, such as a display and a keyboard, for displaying information to the user and for receiving settings and function commands from the user.

For synchronization of the thermal chart with the movement of the object to be measured, the data processor 12 is connected with a means measuring the speed of motion of the object. As shown in FIG. 1, said means can be, for example, in contact with the web 11, and it can be a pulse sensor 15 installed in the centre of a roll 14 rotating at a peripheral speed corresponding to the speed of propagation of the web. The pulse sensor 15 is arranged to generate one or more pulses per each rotation of the roll 14. When the peripheral length of the roll is known, it is possible to determine the exact rate of propagation of the web 11 on the basis of the pulses obtained from the pulse sensor 15.

Alternatively, the data processor 12 may obtain the data about the speed of motion required for the synchronization via the data transmission connection 13 from the apparatus controlling the processing of the web 11, such as, for example, the control system of the paper machine. It will be obvious for anyone skilled in the art that the synchronization data for synchronizing the imaging can, if necessary, also be transferred in a suitable format directly to the thermal camera 10, wherein the synchronization pulse or the like will directly control the operation of the thermal camera 10.

The thermal camera 10 can be arranged to image the web 11 (or another object) across the whole production width of the web in the cross-machine direction, or the imaging can also be focused on a narrower range than the production width. In the cross-machine direction, it is also possible to use several thermal cameras in parallel, to cover the whole production width. Furthermore, the image produced by several cameras can be combined to a single "full-width" two-dimensional thermal chart in the data processor 12.

FIG. 1 shows, in addition to the thermal camera 10 in position A, also two other positions B and C for the use of the thermal camera schematically with broken lines.

In the position B in FIG. 1, the thermal camera 10 is arranged to image the surface of a roll 16 in synchronization with the rotational speed of the roll 16 in such a way that a continuous thermal chart about the surface of the roll 16 is recorded in the data processor 12. Thanks to the synchronization, it is possible to distinguish a section corresponding to each single rotation of the roll 16 as a so-called matched two-dimensional thermal chart, i.e., a thermal chart illustrating the surface of said roll. In such successive matched thermal charts, the same specific point in the two-dimensional thermal chart will thus always correspond to the same specific point on the surface of the roll 16. The matched thermal charts can further be analyzed with the data processor 12, for example, by averaging said thermal charts by averaging the thermal values corresponding to the same point in the object in successive matched thermal charts with each other.

In the position C of FIG. 1, the thermal camera 10 is arranged to image the surface of a moving texture 17 interacting with the web 11 in a way synchronized with the speed of rotation of the texture 17. The texture 17 can be, for example, a so-called drying felt or wire. According to the invention, a continuous thermal chart is now formed in the data processor 12 in the same way as above. From this continuous thermal chart, it is further possible to distinguish single matched surface thermal charts corresponding to one rotation of the web 17, for a more detailed analysis and/or for averaging.

In the following, we shall describe in more detail the analysis of thermal charts formed according to the invention, with reference to FIGS. 2 to 4.

FIG. 2 shows schematically a continuous thermal chart 20 according to the invention. In this example, the thermal chart can be thought as being formed by a thermal camera 10 placed in position A in FIG. 1 and by synchronizing the imaging with the movement of the web 11. The thermal chart 20 thus illustrates the temperature distribution of the surface of the web 11 along a specific known length of the web 11.

In the continuous thermal chart 20, the areas marked with black ovals 21 and black rectangles 22 as well as light circles 23 of different sizes indicate points at which the temperature detected by the thermal camera 10 differs within the measuring accuracy from the temperature of the background 24 illustrated as white. When the object to be imaged is, as shown in FIG. 1, a moving web 11, said areas 21, 22, 23 detected in the thermal chart can be points different from other areas surrounding them in the web 11 with respect to their moisture, material thickness, composition or other properties having the result that the radiation (temperature) emitted by them in the infrared range is different from the background 24.

The smallest detectable temperature differences between the areas 21, 22, 23 and the background 24 can be, depending on the sensitivity of the thermal camera 10 and the measuring situation, for example in the order of fractions of a Kelvin or a few Kelvin.

It is obvious that in reality, the background 24 of the thermal image 20 consists of a large number of points and areas differing from each other to some extent in their brightness level (or temperature). Similarly, for example recurrent areas 21 marked with black ovals do not recur in exactly the same size and brightness level at different parts of the thermal chart 20. Primarily for reasons of the drawing technique and clarity, the background 24 and the areas 21, 22, 23 in FIG. 2 are illustrated with simplified shapes and brightness levels.

In this example, the areas 21 recurring in the continuous thermal chart 20 of FIG. 2 are caused by local damaging/soiling 21' of the coating of the roll 16 shown in FIG. 1. In a corresponding manner, the areas 22 are caused by local damaging/soiling 22' of the texture 17 shown in FIG. 1. The areas 23 indicate minor random temperature changes occurring in the web 11 for various reasons.

According to the invention, the continuous thermal chart 20 can now be analyzed by dividing it into matched thermal charts and further by averaging the matched thermal charts with each other. The cycle length of the matched thermal charts, corresponding to the direction of propagation of the web 11, is selected on the basis of the part or means with which the web 11 is in contact in its path and about which more information is needed.

FIG. 3 shows an averaged matched thermal chart 30 which is formed by dividing the continuous thermal chart 20 in partial charts 27 having the length of a cycle 25. In this case, the length of the cycle 25 corresponds to the peripheral length of the roll 16.

To form the averaged and matched thermal chart 30, the partial charts 27 are averaged together in such a way that the points corresponding to the same pixel in successive partial charts 27 are averaged together. In other words, in this example, the same pixel in the successive partial charts 27 always corresponds to the same point on the surface of the roll 16. In the matched thermal chart 30 obtained as a result of the averaging, the temperature deviation caused by damaging/soiling 21' of the roll 16 is detected as a distinctive area 21''' whose temperature differs from the temperature of its environment. However, local damaging/soiling 22' of the texture 17 is detected as a weaker, streak-like phenomenon occurring across the whole averaged thermal chart 30. The reason for this is that because the peripheral length 25 of the roll 16 is used as the cycle length in the averaging, the cycle of occurrence of the damaging/soiling 22' of the texture 17 does not correlate with said cycle length 25.

FIG. 4 shows an averaged and matched thermal chart 40 formed in a corresponding manner by dividing the continuous thermal chart 20 into partial charts 28 according to a cycle length 26. The cycle length 26 correlating with the cycle of occurrence of damaging/soiling 22' of the texture 17, the corresponding temperature deviation 22''' is now clearly visible in the averaged thermal chart 40. In this situation, the change in temperature caused in the averaged and matched thermal chart 40 by areas 21 occurring at cycle lengths 25 in the continuous thermal chart 20 is, in turn, distributed in a corresponding manner over the area corresponding to the whole length of the thermal chart 40.

Temperature deviations 23 which occur at random in the continuous thermal chart 20 and do not correlate with the cycle lengths 25, 26 used in the formation of matched thermal charts are levelled out in the averaged thermal charts 30 and 40 as backgrounds 31 and 41. Using a sufficiently long averaging, it is thus possible, in the method according to the invention, to efficiently reduce random noise occuring in thermal charts. Such random noise occurs, for example, in a situation, in which the imaging is disturbed by water mist or water spraying occurring between the camera 10 and the object to be imaged. Such a situation is typical when the imaging is performed, for example, in the wet end of the paper machine.

Consequently, the method according to the invention makes it possible to detect the cause of phenomena detectable at a measuring object, such as web 11, on the basis of the recurrence of said phenomena. The phenomena may be caused by means located immediately before the measuring point, or also by means located farther away from the measuring point. Typically, a "mark" caused in the web 11 by a means located farther away from the measuring point is, to some extent, faded when arriving at the measuring point; therefore, its detection will typically require the longer averaging, the farther away from the measuring point the means causing the mark is located.

Using infrared imaging according to the invention, it is still possible to detect a mark caused in the web by a previous means, also when said means is relatively far away, thanks to the good sensitivity of the infrared measurement.

Although the invention has been described above primarily for the purpose of detecting transient spot-like defects in the direction of movement of the object to be measured, it is obvious that the invention can also be used to detect various streak-like defects of longer duration in the direction of movement. In a streak-like defect, which is continuous in the direction of movement, the recurrence of the defect in the direction of movement and thereby the cause of the defect can be identified, for example, as recurrent variation in the width of the streak and/or as recurrent "twisting" of the streak in the direction transverse to the direction of movement. In discontinuous streaks, i.e. streaks occurring as stretches, the recurrence can be identified, for example, on the basis of the moments of starting and/or ending of the streak.

Further, the defects detectable by means of the method can be, in the same way as spots, narrow in the cross-machine direction, or the defects can also extend to a wider range in the cross-machine direction, all the way to the production width. Wider defects in the cross-machine direction which are detectable by the method may include, for example, whipping of the web which will be discussed in more detail in connection with the embodiments of the invention hereinbelow.

Thus, the only precondition which is substantial in view of the invention is primarily that some kind of recurrence in the direction of movement can be identified in the defect to be detected on the basis of a local deviation in temperature, to determine the cause of the defect.

Preferably, the measurement according to the invention is made in such a way that a portion of the continuous thermal chart 20 with a certain length is recorded in the memory of the data processor 12. After this, the continuous thermal chart 20 stored in the memory is analyzed by dividing it into matched partial charts 27, 28 having the length of a given cycle. The matched partial charts 27, 28 can further be averaged to form averaged and matched thermal charts 30, 40. The cycle length 25, 26 to be used in the formation of matched thermal charts can be selected of predetermined cycle lengths which have been stored in the memory of the data processor 12 and which correspond to the peripheral lengths of different rotating/moving rolls or textures, or the like, in the apparatus to be monitored. The continuous thermal chart 20 is analyzed by using said known different cycle lengths one after the other.

Alternatively, it is also possible that the data processor 12 automatically scans different cycle lengths at a range determined by the user, looking for any cycle length at which an obvious correlation is detected in the averaged and matched thermal chart 30, 40. When such a correlation is detected, an attempt is made to identify its cause on the basis of the corresponding cycle length from the data about the process apparatus stored in advance in the memory of the data processor 12. If necessary, the user is also informed of the correlation.

Naturally, it will be obvious for anyone skilled in the art that the data processor 12 can be implemented in such a way that a continuous thermal chart 20 stored in the memory of the data processor 12 is efficiently processed by using in the computation, for example, several cycle lengths 25, 26 simultaneously in parallel. This can be implemented, for example, by two or more processor circuits operating in parallel and analyzing the same continuous thermal chart 20 stored in the memory, by different methods. Further, the data processor 12 can also be implemented in such a way that when analyzing the continuous thermal chart 20 stored in the memory, the signal generated by the thermal camera 10 is simultaneously stored in another location in the memory of the data processor 12, wherein no measuring information produced by the camera 10 is lost during said analysis. Said embodiments make it possible to produce measuring information about the object to be measured substantially in real time, which will further make it possible to quickly intervene in the process to be monitored, automatically or manually by the user.

Embodiments of the Invention

In the following, we shall present some embodiments exemplifying the application of the method according to the invention in processes of manufacturing and/or finishing paper, board, or a corresponding material.

A local blockage or damage in a texture used for drying a fibre web, such as a drying felt, can be detected by direct imaging of the surface of the drying felt. Thus, a local deviation in the temperature (moisture) will be detected in the matched thermal chart of the felt recorded during its single rotation, or in a matched and averaged thermal chart computed on the basis of several rotations. The same malfunction of the drying web can also be detected on the basis of the recurrent "marking" of the drying web in the passing fibre web, by imaging the fibre web to be processed. At the point of the fibre web corresponding to the blocked point in the felt, or the like, the moisture of the web differs from the moisture in the surrounding area of the web, which is detected as a temperature difference in the thermal image. The farther away from the component causing the defect the imaging of the web takes place, the longer the averaging which is typically required to detect the phenomenon, because it fades as the distance becomes longer.

By imaging the drying felt or another texture interacting with the web, or the marking caused by said texture in the web, it is also possible to detect, for example, malfunctions of water sprays cleaning said texture, and/or defects in the cross-machine profile of the press section pressing the texture and the web against each other. Typically, a defect in the cross-machine profile of the nip between two opposite rolls in the press section may be caused, for example, by curving of the rolls in the direction of the longitudinal axis (incorrect crowning) or by dirt or other material adhered locally to the surface of the rolls.

The effect of nip vibrations, i.e. unfavourable temporal changes in the nip force, can be detected in thermal imaging as so-called whipping of the texture or the web to be processed, passing through the nip. Whipping refers to the formation of stripes in the cross-machine direction in the object to be imaged, caused by temporal variations in the nip force and thereby further, for example, variations in the drying capacity. The cycle length of nip variations is typically significantly shorter than the peripheral length of the rolls forming the nip.

The textures used in manufacturing and/or finishing processes of paper and/or board, in connection with which the method of the invention can be applied, include not only the above-mentioned drying felt but also various wires and belt rolls. By means of the invention, it is also possible to detect obstructions in the suction roll on the basis of marking caused by the suction roll in the fibre web, by synchronizing the measurement of the fibre web with the rotation of the suction roll.

The method of the invention is also suitable for controlling the condition of so-called soft rolls. Soft rolls are used, for example, in the calendering of paper, wherein the paper web is guided through one or more so-called calender nips. The calender nip is formed between a hard-faced metal roll and a soft-faced roll. The nip can also be formed between two soft-faced rolls. In soft-faced rolls used in modern calenders, the metal roll frame is typically coated with a polymer material. The polymer coating of the roll may be damaged during the use, for example, when extra solid material is passed through the nip, causing a momentary and local increase in the nip force, a kind of a pressure impact which damages the roll coating locally. The coating damage can also be caused by the temperature of the coating which increases, for some reason, locally to a too high level for the polymer material used. Factors affecting the temperature of the coated roll include, for example, a change in the heat transfer properties caused by a dirt layer adhered to the roll, or other changes in the nip contact, particularly when heated backing rolls are used.

Using the method according to the invention, the condition of the soft-faced roll can be monitored by imaging the surface of the roll in synchronization with the rotation speed of the roll and thereby forming a matched two-dimensional thermal chart of the surface of the roll in accordance with the invention. If necessary, several matched charts corresponding to one rotation of the roll can be averaged, as described above. Defects in the roll coating are detected, for example, as areas hotter than the surrounding roll coating, as so-called hot spots, as whipping of the roll coating, or as variations across the whole width of the roll in the machine direction.

Applying the method of the invention, it is also possible to detect, in connection with coated rolls, such transient phenomena which cannot be properly detected by methods of prior art. Such phenomena include, for example, in connection with a coated paper web, local variations in the quantity of coating material carried by the paper web onto the roll, that is, so-called wet coating spots, coating streaks or other transient coating defects. When passing through the calender nip and adhering to the coated roll, such coating defects may cause not only a variation in the quality of the final product but also direct damage to the roll coating.

When applying the method of the invention, it is possible to detect such a problematic situation quickly and thereby to reduce the probability of causing a coating defect or to prevent the coating damage from becoming worse. Quick detection of the problematic situation will also reduce the production of a final product of poor quality.

By means of information obtained about the condition of the coated roll substantially in real time, it is also possible to design the maintenance of the rolls better and to avoid unforeseen and unnecessary stoppages. The condition of the roll coatings can also be controlled by measuring the fibre web to be processed, wherein defects occurring in roll coatings are detected by means of recurrent marking of the fibre web. The control by imaging of the fibre web has the advantage that measurements made at one measuring point can thus be used to control a longer web length. For example, in a calender, the condition of several soft rolls can be monitored by means of one measuring point placed after the calender.

By means of the present invention, it is thus possible to control, in a considerably more versatile way than before, various properties of components used in processes for manufacturing or finishing a fibre web, as well as properties of the web to be manufactured or finished.

According to the need, various essential steps of the process can each be provided with a separate thermal camera/cameras which can be in use either full time or also periodically.

At a certain point of measurement, the imaging width can be suitably selected according to the resolution of the camera. The imaging can be performed in a direction transverse to the direction of movement of the object, for example for an area with the width of one metre, which area is moved in the transverse direction alternatively at different locations of the production width. Momentarily, the imaging can be zoomed to take place across the full width of the web, wherein it is also possible to detect wider deviations in the cross-machine direction.

Thanks to the synchronization with the movement of the object to be imaged, the method of the invention can also be applied in a situation in which the movement of the object is accelerating or decelerating.

By combining the modes and apparatus structures presented in connection with the different embodiments of the invention presented above, it is possible to provide various embodiments of the invention which comply with the spirit of the invention. Therefore, the above-presented examples must not be interpreted as restrictive to the invention, but the embodiments of the invention can be freely varied within the scope of the inventive features presented in the claims hereinbelow.

What is claimed is:

1. A method in the process of manufacturing and/or finishing a fibre web, in which method said continuous and moving web, is monitored in a time-resolved manner and in synchronization with the movement of the web by one or more thermal cameras of the infrared range or with a corresponding detector/detectors for the purpose of controlling the quality or condition, said method comprising the steps:

in the direction of the movement of the web, a continuous two-dimensional thermal image, i.e. a continuous thermal chart of the web is formed by said detector/detectors for analyzing the formed continuous thermal chart, the continuous thermal chart is divided into successive matched partial charts where the cycle length used in forming the partial charts is selected to correspond to the length of influence specific to the means related to the processing of the passing web and for detecting the malfunctioning of the means related to the processing of the web on the basis of a periodical marking caused by said means in the passing web, local deviations and/or discontinuities particularly in the direction of movement of the web in the temperature are detected from the said matched partial charts.

2. The method according to claim 1, wherein the cycle length to be used in the formation of the partial charts is selected to correspond to the length of the periphery/shell in the direction of movement of the progressing or rotating means related to the processing of the web.

3. The method according to claim 1, wherein the cycle length to be used in the formation of the partial charts is selected to correspond to the length of influence specific to the vibration or corresponding interference in the means related to the processing of the web.

4. The method according to claim 1, wherein the cycle length to be used in the formation of the partial charts is selected from a range determined by the user, looking for such a cycle length, with which a distinct deviation and/or a discontinuity in the temperature is detected in the matched partial chart.

5. The method according to claim 1, wherein successive matched partial charts are combined to an averaged and matched thermal chart to improve the sensitivity of the method and/or to reduce the effect of random interference.

6. The method according to claim 1, wherein the continuous thermal chart is formed of unidimensional temperature profiles recorded at successive moments of time in the direction transverse to the direction of its movement, said temperature profiles being measured by a scanning device or a device based on the use of a line indicator.

7. The method according to claim 1, wherein the continuous thermal chart is formed of two-dimensional thermal images of a web recorded at successive moments of time, said thermal images being measured by a device based on the use of a two-dimensional matrix indicator.

8. The method according to claim 1, wherein the continuous thermal chart or matched partial charts defined from it are formed over the whole or only a part of the width of the web or means related to web handling object to be monitored in the direction transverse to the direction of movement of the object.

9. The method according to claim 1, wherein the continuous thermal chart is formed by using a detector operating in the infrared wavelength range of 3 to 12 micrometres or in one or more narrower wavelength bands within said range.

10. The method according to claim 1, wherein the method is used for monitoring a texture, such as a wire or a felt, used in connection with the processing of the web.

11. The method according to claim 1, wherein the method is used for monitoring a roll or roll coating used in connection with the processing of the web.

12. The method according to claim 1, wherein the method is used for monitoring a suction roll used in connection with the processing of the web.

13. The method according to claim 1, wherein the method is used for monitoring a reel or the like formed of the web.

14. The method according to claim 1, wherein on the basis of phenomena detected by the method, the process of manufacturing and/or finishing the web is adjusted by the user or automatically.

15. The method according to claim 1, wherein on the basis of phenomena detected by the method, the need for maintenance of the means and components used in the process of manufacturing and/or finishing the web is evaluated by the user or automatically.

* * * * *